United States Patent
Quijano et al.

(10) Patent No.: US 6,830,586 B2
(45) Date of Patent: Dec. 14, 2004

(54) STENTLESS ATRIOVENTRICULAR HEART VALVE FABRICATED FROM A SINGULAR FLAT MEMBRANE

(75) Inventors: Rodolfo C. Quijano, Laguna Hills, CA (US); Than Nguyen, Placentia, CA (US); Hosheng Tu, Newport Coast, CA (US)

(73) Assignee: 3F Therapeutics, Inc., Lake Forrest, CA (US)

( * ) Notice: Subject to any disclaimer, the term of this patent is extended or adjusted under 35 U.S.C. 154(b) by 0 days.

(21) Appl. No.: 10/086,100

(22) Filed: Feb. 28, 2002

(65) Prior Publication Data

US 2003/0163195 A1 Aug. 28, 2003

(51) Int. Cl.[7] ................................................. A61F 2/24
(52) U.S. Cl. ........................ 623/2.13; 623/2.1; 623/2.12
(58) Field of Search ................................ 623/2.1, 2.11, 623/2.12, 2.13, 2.17, 2.36, 2.38, 2.39, 2.4, 2.41

(56) References Cited

U.S. PATENT DOCUMENTS

| | | | |
|---|---|---|---|
| 3,464,065 A | * | 9/1969 | Cromie ................................ 3/1 |
| 4,261,342 A | | 4/1981 | Aranguren Duo |
| 4,790,844 A | * | 12/1988 | Ovil ................................ 623/2 |
| 5,156,621 A | | 10/1992 | Navia et al. |
| 5,344,442 A | | 9/1994 | Deac |
| 5,415,667 A | | 5/1995 | Frater |
| 5,480,424 A | | 1/1996 | Cox |
| 5,500,015 A | | 3/1996 | Deac |
| 5,509,930 A | | 4/1996 | Love |
| 5,554,184 A | | 9/1996 | Machiraju |
| 5,662,704 A | | 9/1997 | Gross |
| 5,713,950 A | | 2/1998 | Cox |
| 5,824,063 A | | 10/1998 | Cox |
| 5,824,067 A | | 10/1998 | Gross |
| 5,984,973 A | | 11/1999 | Girard et al. |
| 6,074,417 A | * | 6/2000 | Peredo .......................... 623/2 |
| 6,092,529 A | | 7/2000 | Cox |
| 6,197,143 B1 | * | 3/2001 | Bodnar ........................ 156/218 |
| 6,214,055 B1 | | 4/2001 | Simionescu et al. |
| 6,254,642 B1 | * | 7/2001 | Taylor ..................... 623/23.64 |
| 6,270,526 B1 | | 8/2001 | Cox |
| 6,312,464 B1 | | 11/2001 | Navia |
| 6,342,070 B1 | | 1/2002 | Nguyen-Thien-Nhon |
| 6,358,277 B1 | * | 3/2002 | Duran ........................ 623/2.12 |
| 6,368,348 B1 | * | 4/2002 | Gabbay ..................... 623/2.36 |

OTHER PUBLICATIONS

A Angelini et al., "Anatomy of the Mitral Valve", chap 1 in Mitral Valve, edited by H Boudoulas and CF Wooley, published by Futura Publishing Company NY 2000.

* cited by examiner

*Primary Examiner*—Bruce Snow
*Assistant Examiner*—Cheryl Miller
(74) *Attorney, Agent, or Firm*—Jones Day

(57) ABSTRACT

A stentless atrioventricular valve intended for attaching to a circumferential valve ring and papillary muscles of a patient comprising a singular flexible membrane of tissue or synthetic biomaterial, the valve having a sewing ring, an anterior cusp and a posterior cusp, wherein the anterior cusp and said posterior cusp are an integral part of a continuum from the singular membrane without sutured commissure between remote ends of the cusps and wherein texture elements secured at edge portions of the cusps configured to extend the texture elements for connection to papillary muscles in a ventricle cavity when the sewing ring is sutured to an atrioventricular junction of a patient's heart.

3 Claims, 11 Drawing Sheets section I-I

FIG. 10 section I-I

STENTLESS ATRIOVENTRICULAR HEART VALVE FABRICATED FROM A SINGULAR FLAT MEMBRANE

FIELD OF THE INVENTION

The invention herein described relates to cardiac atrioventricular valves, specifically to a valve apparatus fabricated for replacement of human mitral or tricuspid heart valves from a singular membrane of tissue or synthetic plastic.

BACKGROUND OF THE INVENTION

Replacement heart valves have been fabricated or manufactured for the last forty years. Such devices have been assembled from a variety of materials. Specifically the materials have been of biologic or artificial nature, generally leading to two distinct categories of the prostheses as biological or mechanical replacement heart valves.

The prosthetic heart valves are fabricated to replace the natural heart valves that, because of disease, congenital malformations, ageing or trauma have become dysfunctional and require repair to their functional elements or partial or complete replacement. Characteristics for a desirable prosthetic heart valve may include hemodynamic performance, thrombogenicity, durability and ease of surgical implantation.

Human heart valves under the conditions of normal physiological functions are passive devices that open under the pressure of blood flow on their leaflets. There are four valves in the heart that serves to direct the flow of blood through all chambers in a forward direction. In general, blood leaves the heart lower chambers in the direction to the rest of the body or to the lungs for required oxygenation, or blood enters the lower chambers from the upper chambers of the heart. Similarly, they close under the pressure exerted on the same leaflet elements when blood flow is retrograde, thus impeding return of blood flow to the chamber it has just left. This, under normal conditions, (that is, when the body is not under physical stresses and the heart is beating at the normal resting state of about 70 beats per minute) equates to the leaflets opening by separation from each other, thereby producing an opening or closing by apposing to each other approximately 38 million times per year. It can be surmised that under stress conditions this may be happening at higher rates, thus increasing the number of separations and appositions, as well as the forces of impact between the leaflets during the closing.

When disease conditions affect the structure of the materials of the components of the valve apparatus, the valve itself will decay, degenerate or disrupt and require repair or replacement to restore proper function necessary for the continuation of life.

The shape of the leaflet and surrounding elements of a valve or a valve apparatus is dependent on the function of the heart. While in the past numerous publications taught that the preformed valve directs the function, new paradigms have explained that it is the function of the heart that in actuality directs and defines the formation of the specific shape or form of the valve. This, the principle of "Form Follows Function" can be used to produce new valvular mechanisms that more closely approximate the function of the native human heart valves.

In the case of the atrioventricular valves, otherwise known as mitral (in the left lower chamber of the heart) and tricuspid (in the right ventricle), the valve is part of a continuum that extends from the myocardium or muscular wall of the lower chambers, through the papillary muscles, to which is attached a confluence of tendinous rope-like elements known as chordae tendinae that themselves are attached to the edges of differently shaped leaflets which form the flow-allowing and flow-stopping or obstructing elements (leaflets). These leaflets continue and end at a ring-like structure usually known as annulus, that is part of the skeleton of the heart. It is this continuum which should be called an apparatus rather than just valve.

Thus, there is a tricuspid valve apparatus in the right ventricular chamber, and more importantly the mitral valve apparatus within the lower left heart chamber or left ventricle, the pumping function of which provides the systemic flow of blood through the aorta, to keep all tissues of the body supplied with oxygenated blood necessary for cellular function and life. Hence during the cardiac cycle, the valves function as part of a unit composed of multiple interrelated parts, including the ventricular and atrial walls, the valve leaflets, the fibrous skeleton of the heart at the atrioventricular ring, and the subvalvular apparatus. The subvalvular apparatus includes the papillary muscle within the ventricle, and the chordae tendinae which connect the papillary muscle to the valve leaflets.

The present practice of valvular surgery when mitral valve alone is replaced after excision of the diseased mitral valve apparatus ignores the necessary contribution of the ventricular function. Ventricle and apparatus work in unison to provide proper pumping to systemic or pulmonary circulation and proper arrest of blood return to the atrial chambers.

Aortic and pulmonary valves have been replaced with simple trileaflet chemically treated biological valves obtained from animals, or bileaflet mechanical valves without extreme deficiencies in valvular or cardiac function. This is not the case when mitral or tricuspid valves are replaced and the necessary involvement of chordae tendinae and muscular element of the chamber wall are not united to function in harmony with the valve leaflets. Those valves used in the aortic position cannot alone replace the mitral valve apparatus without anatomical and functional compromise.

Therefore, this requirement to maintain said continuum is of an absolute imperative nature for the mitral or tricuspid valve apparatus.

In the past, attempts to generate the needed structure have met with difficulties. Thus, Aranguren Duo in U.S. Pat. No. 4,261,342, Gross in U.S. Pat. No. 5,662,704, and Gross in U.S. Pat. No. 5,824,067, incorporated herein by reference in their entirety, resort to use of a pig heart (porcine, swine) mitral valve to which a covering material is attached to the papillary heads around the chordae tendinae, in the form of a tube that provides an extension in order to fit and affix the valve to the papillary muscle remnants of the human heart after the diseased valve and subvalvular structure is excised and removed from the heart. This tube has to be trimmed until the proper dimension is found to connect the leaflets to the papillary remnants. However, trimming the tube during the surgery is necessary because the relation between annular size and chordal length are different in animal than in human hearts.

Frater in U.S. Pat. No. 5,415,667 teaches an apparatus with a trapezoidal annulus possessing a rigid side. To this trapezoidal annulus are attached four separate leaflets joined together by sutures to provide an occluding surface to the flow of blood during the systolic or ejection phase of the cardiac cycle. The chordae are separate chords attached by sewing to the edge portion of the leaflets though at times are integral of the four separate cusps and each attached by sewing the other three cusps. All four cusps and their respective chordal attachment portions and flange portions are formed as separate components for fitting to a basic ring element having a trapezoidal opening. The sutured attachment portions render the cusp less flexible as compared to a natural cusp without sutures.

Machuraju in U.S. Pat. No. 5,554,184 discloses cutting two leaflets that are then sutured together to form a bileaflet valve. Similarly, Deac in U.S. Pat. No. 5,344,442 and U.S. Pat. No. 5,500,015, entire disclosures of which are incorporated herein by reference, teaches means for cutting sections of biological material and joins them by sutures to form a bileaflet mitral valve. The sutured joint portion becomes stiff and less flexible. There is a clinical needs to fabricate a bileaflet or trileaflet valve with sutureless joint portion or commissure; preferably to have the valve made from a singular membrane of tissue or artificial sheet.

All of the aforementioned patents teach of a form made by stitching various sections of material and expecting that the form will be able to profile the function. This leads Cox in U.S. Pat. No. 6,270,526 to pronounce his principle of "Form Follows Function". He notices that the human foetus while in its early stages (about 25 days of gestation) in utero that further exhibits tubular connections between the foetal heart gestational developments will produce the structure. This "Form Follows Function" is the paradigm that must be used in order to fabricate a heart valve that will very closely identify with the human heart valve.

Current Options for Tissue Heart Valve Replacement

Most tissue valves are constructed by sewing the leaflets of pig aortic valves to a stent to hold the leaflets in proper position as a stented porcine valve. They may also be constructed by removing valve leaflets from the pericardial sac of cows or horses and sewing them to a stent as a stented pericardium valve. The stents may be rigid or slightly flexible and covered with cloth (usually a synthetic material sold under the trademark Dacron™ or Teflon™) and attached to a sewing ring for fixation to the patient's native tissue. In one embodiment, the porcine, bovine or equine tissue is chemically treated to alleviate any antigenicity.

A stentless valve prosthesis generally comprises a biological valve having a suture ring, anchoring skirts at the commissures of the valve, and an outer polyester covering. A stentless valve prosthesis secured to the native valve annulus and leaflets reduces tissue stress as the flexible valve prosthesis adapted and conforms to the native valve, so that durability and resistance to wear and calcification are improved.

The main advantage of tissue valves is that they do not cause blood clots to form as readily as do the mechanical valves, and therefore, the tissue valves do not typically require life-long systemic anticoagulation. However, the presence of the stent and sewing ring prevents the tissue valve from being anatomically accurate in comparison to a normal heart valve.

Principles of Tissue Heart Valve Construction

Cox in U.S. Pat. Nos. 6,270,526, 6,092,529, 5,824,063, 5,713,950, and 5,480,424, incorporated herein by reference in their entirety, teaches the "function follows form" principles of tissue heart valve construction. Under the best of circumstances (i.e., replacement of the aortic valve), the construction of artificial tissue valves has been based on the concept that if the artificial valve can be made to approximate the anatomy (form) of the native valve, then the physiology (function) of the artificial valve will also approximate that of the native valve. This is the concept that "Function Follows Form." For example, the manufacturers of all artificial porcine valves first re-create the form of a native human aortic valve by: 1) harvesting a porcine aortic valve, 2) fixing it in glutaraldehyde or other suitable fixatives to eliminate antigenicity, and 3) suturing the porcine valve to a stent to hold the three leaflets in place. In other words, the primary goal in the construction of these artificial valves is to reproduce the form of the human aortic valve as closely as possible. The assumption is made that if the artificial valve can be made to look like the human aortic valve, it will function like the human aortic valve (i.e., proper function will follow proper form). The same assumption is also followed for commercially available pericardial valves.

In the case of mitral or tricuspid valve replacement, even the dubious concept of "function follows form" has been discarded since the same artificial valves that are designed to look like the aortic valve are used to replace the mitral and tricuspid valves. In other words, no attempt at all is made to reproduce even the form of these native valves, much less so their function.

Thus, in the case of artificial valves to be used for aortic valve replacement, the dubious concept of "function follows form" has dictated the construction of all artificial tissue valves during the 30 years of their development and use. Even worse, no discernable underlying concept at all has been used in terms of the artificial valves used to replace the mitral and tricuspid valves.

The "Function Follows Form" concept has several limitations and appears to be a fundamental shortcoming which underlies the present construction of all artificial tissue valves. In the first place, it simply is not possible to recreate the exact anatomy (form) of a native heart valve utilizing present techniques. Although homograft (human cadaver) and porcine aortic valves have the gross appearance of native aortic valves, the fixation process (freezing with liquid nitrogen, and chemical treatment, respectively) alters the histological (microscopic) characteristics of the valve tissue. Porcine and bovine pericardial valves not only require chemical preparation (usually involving fixation with glutaraldehyde), but the leaflets must be sutured to cloth-covered stents in order to hold the leaflets in position for proper opening and closing of the valve. A recent advance has been made in this regard by using "stentless" porcine valves that are sutured directly to the patient's native tissues for aortic valve replacement, but the problem of chemical fixation remains. In addition, these stentless artificial valves cannot be used for mitral or tricuspid valve replacement.

Perhaps the major limitation of the "Function Follows Form" concept is that no efforts have been made previously to approximate the form of either the mitral valve or the tricuspid valve. If animal tissue valves are used to replace either of these native valves, the tri-leaflet porcine aortic valve prosthesis or the tri-leaflet bovine pericardial valve prosthesis is normally used. In doing so, even the faulty concept of "Function Follows Form" is ignored, since there are no artificial valves available for human use that approximate the anatomy (form) of the native mitral or tricuspid valves.

The object of the present invention is to fabricate a stentless atrioventricular valve that avoids the aforementioned disadvantages, wherein the valve comprises a singular membrane of biocompatible material that has at least two cusps configured to form a substantially tubular shape for use as an atrioventricular valve.

SUMMARY OF THE INVENTION

It is one object of the present invention to provide a stentless atrioventricular valve comprising a singular membrane of tissue or plastic material. In one embodiment, the valve has a sewing ring and at least two cusps hinged continuously from the inner opening of the sewing ring, wherein the cusps are an integral part of a continuum from the singular membrane configured or conformed to form a substantially tubular shape for use as an atrioventricular valve. In one embodiment, the substantially tubular form of the disclosed stentless atrioventricular valve follows the "Function Follows Form" concept.

It is another object of the present invention to fabricate a stentless atrioventricular valve with singular membrane of tissue biomaterial that is chemically treated to reduce its antigenicity. Alternately, the singular membrane of biomaterial of the present invention is a synthetic plastic.

It is still another object of the present invention to provide a method of forming a stentless atrioventricular valve intended for attaching to a circumferential valve ring and papillary muscles of a patient comprising a singular membrane of biomaterial with at least two cusps, wherein either cusp has a semicircular tip edge joined by two generally straight side edges and wherein each straight side edge is trimmed and configured at an angle of about less than 20 degrees from a reference imaginary central longitudinal line of that cusp.

In one embodiment, the sewing ring is made from a continuum of the singular membrane or is further supported by a sewing ring element to enhance the attachment of the sewing ring onto a heat valve annulus of a patient. In an alternate embodiment, the sewing ring element is made of a biocompatible material selected from a group consisting of non-biodegradable plastic material, biodegradable plastic material, non-biodegradable biological material, biodegradable biological material, and the like.

In another embodiment, the cusps further comprise texture element(s) at an edge portion of the cusps configured and adapted to extend the texture elements for connection to papillary muscles in a ventricle cavity when the sewing ring is sutured to an atrioventricular junction of a patient heart. In a further embodiment, the texture elements may be made of polyester, polytetrafluoroethylene fabric, polyurethane, silicone, or other suitable fabrics.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 11, what is shown is an embodiment of a stentless atrioventricular valve comprising a singular membrane of tissue or plastic biomaterial. Specifically, the stentless atrioventricular valve of the present invention comprises an anterior cusp and a posterior cusp, each cusp having two generally straight side edges that are joined at a semicircular tip edge, wherein each of the straight side edges is trimmed and configured at an angle of about 20 degrees or less, preferably between a range of 15 to 20 degrees, from a reference central longitudinal line of the cusp.

Figure 1:
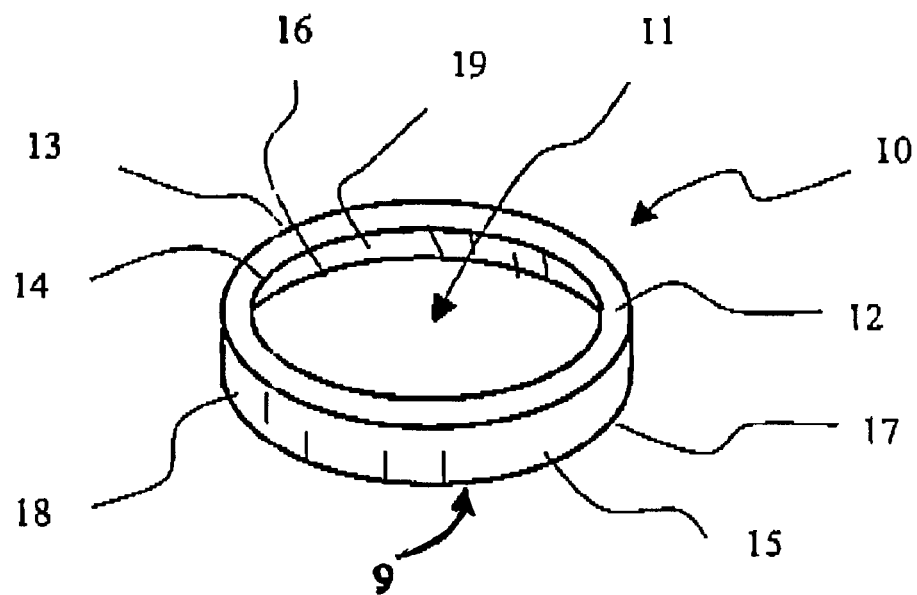
FIG. 1 is a sewing ring element comprising essentially flat side surfaces to be wrapped within a singular membrane of biomaterial for valve fabrication.

An atrioventricular heart valve made of a singular flexible membrane is described as follows. FIG. 1 shows a sewing ring element comprising essentially flat or straight side surfaces to be wrapped within a singular membrane of biomaterial for valve fabrication of the present invention. A sewing ring element 10 having a general configuration of circular, oval shape, or D-shape may be made of rigid, semi-rigid or flexible biomaterial from synthetic polymer or biological tissue. In one embodiment, the sewing ring element 10 in FIG. 1 comprises a first top surface 12 bordered by a first inner edge (that is, the inner perimeter) 14 defining the ring opening 11 and a first outer edge 13 (that is, the outer perimeter), a second bottom surface 15 opposite of the first surface 12, wherein the first surface 12 and the second surface 15 are connected by a supporting member of the sewing ring element 10. The second surface 15 is bordered by a second inner edge (that is, perimeter) 16 defining the bottom ring opening 9 and a second outer edge or perimeter 17.

In one embodiment, the ring opening 11 at the first top surface 12 is identical in shape and size to the bottom ring opening 9. The ring 10 is conformed suitable for suturing or securing onto another material, such as a singular flexible membrane 20 of the present invention. In a particular embodiment, the configuration or shape of the first inner edge 12 may not necessarily match that of the second inner edge 16 while the configuration or shape of the first outer edge 13 may not necessarily match that of the second outer edge 17. The sewing ring opening of the present invention may be "D" shaped and matched by a correspondingly larger D-shaped external profile suitable for placing the atrioventricular valve in a patient heart. A circular, oval shaped or D-shaped ring opening that is stentless and flexible for replacing an atrioventricular valve is well known to a cardiac surgeon or skilled artisan.

The sewing ring element 10 further comprises an inner perimeter 14 including at least a straight side portion 19 thereof and an outer perimeter 13 having a straight side portion 18. The side portions 18, 19 may also be a non-straight configuration. In another alternate embodiment, the cross-section configuration of a sewing ring element may be square, circular, oval, D-shaped, trapezoidal, or other irregular shape.

In an illustrative embodiment, the sewing ring element may be made of a biocompatible material selected from a group consisting of non-biodegradable plastic material, biodegradable plastic material, non-biodegradable biological material, or biodegradable biological material. The sewing ring element may be textured, porous, or constructed of fabric components suitable for valve fabrication.

In a particular embodiment, the sewing ring element of the present invention may be a virtual element or a temporary template. The "virtual element" is herein intended to mean an imaginary non-existing element that aids in better describing and assisting the valve fabrication process. The sewing ring element as a temporary template aid is intended to simplify the valve fabrication process, followed by disengaging the template from the finished valve. One example of the temporary template is made of a liquid soluble substance that is disengaged from the valve by dissolution or biodegradation.

Figure 2:
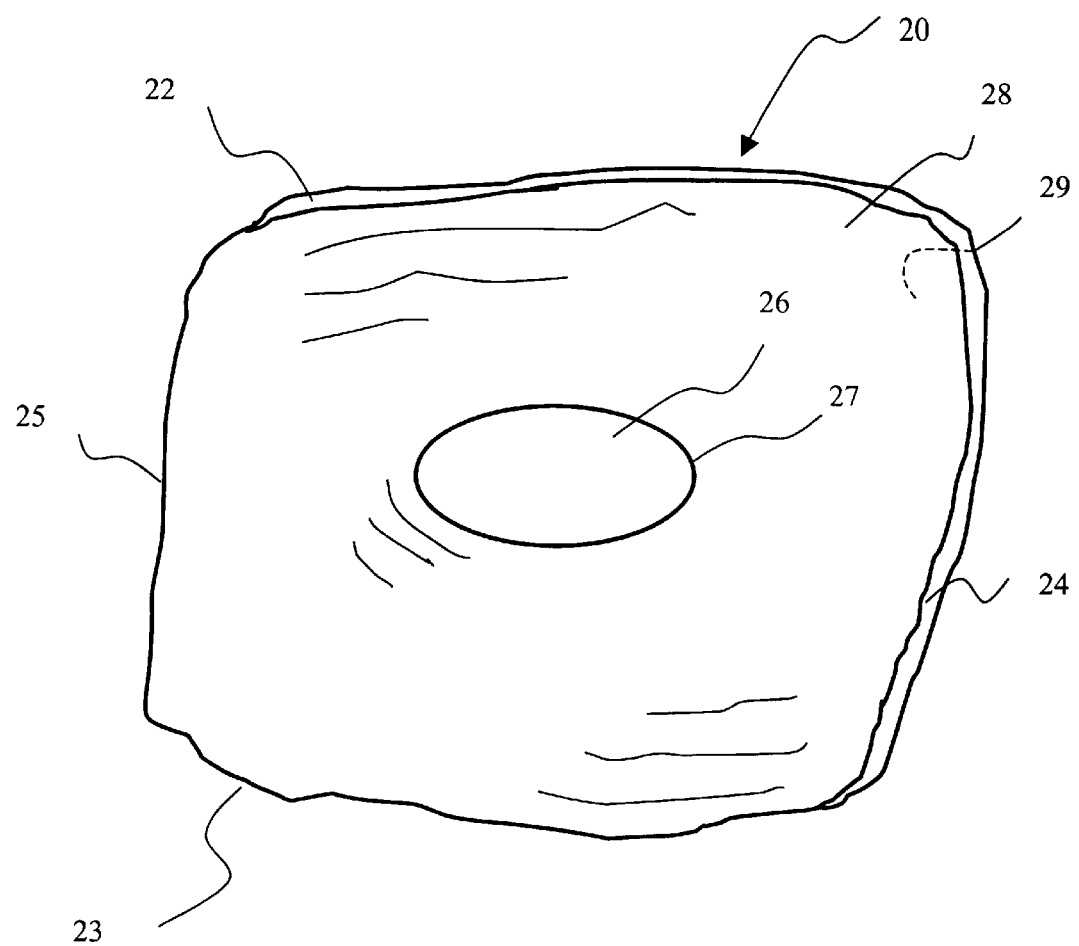
FIG. 2 is a singular membrane of biomaterial having a hole at about a central region of the membrane adapted for valve fabrication of the present invention.

FIG. 2 shows a singular membrane of biomaterial having a hole 26 with its border or perimeter 27 at about a central region of the membrane and a periphery region 35 (shown in FIG. 5) adapted for valve fabrication. The singular flexible membrane 20 has a first membrane surface 28 and an opposite second membrane surface 29. The surface property/morphology of the surface 28 may be similar or different to that of the opposite membrane 29. Typically, the membrane surfaces 28, 29 are relatively smooth for intended valve fabrication purposes. In one embodiment, the membrane 20 is shaped like a typical rectangular singular sheet that is bordered by four edges 22, 23, 24, and 25 that are part of the periphery 35. In an alternate embodiment, the membrane may shape circularly, irregularly without recognizable edges, or in a special design configuration. The membrane 20 may be selected from biological tissue, a synthetic polymer or a synthetic protein matrix. The membrane of biological tissue may be chemically treated to reduce its antigenicity. The chemicals for treating biological tissue may include glutaraldehyde, formaldehyde, dialdehyde starch, polyepoxy compounds, or the like that are well known to one who is skilled in the art of chemical treatment. Further, the membrane of tissue may be pericardium tissue selected from a group consisting of equine, bovine, porcine, ovine, human, or other animals. The thickness of tissue membrane is preferred to be in the range of less than 0.1 mm up to about a few millimeters. The singular membrane 20 made of synthetic polymer may be selected from a group consisting of polyurethane, silicone, expanded polytetrafluoroethylene, fluoro-polymer, polyester, polyethylene, polypropylene or co-polymer thereof. The singular membrane of the present invention has adequate strength or mechanical properties suitable as a heart valve construct.

Figure 3:
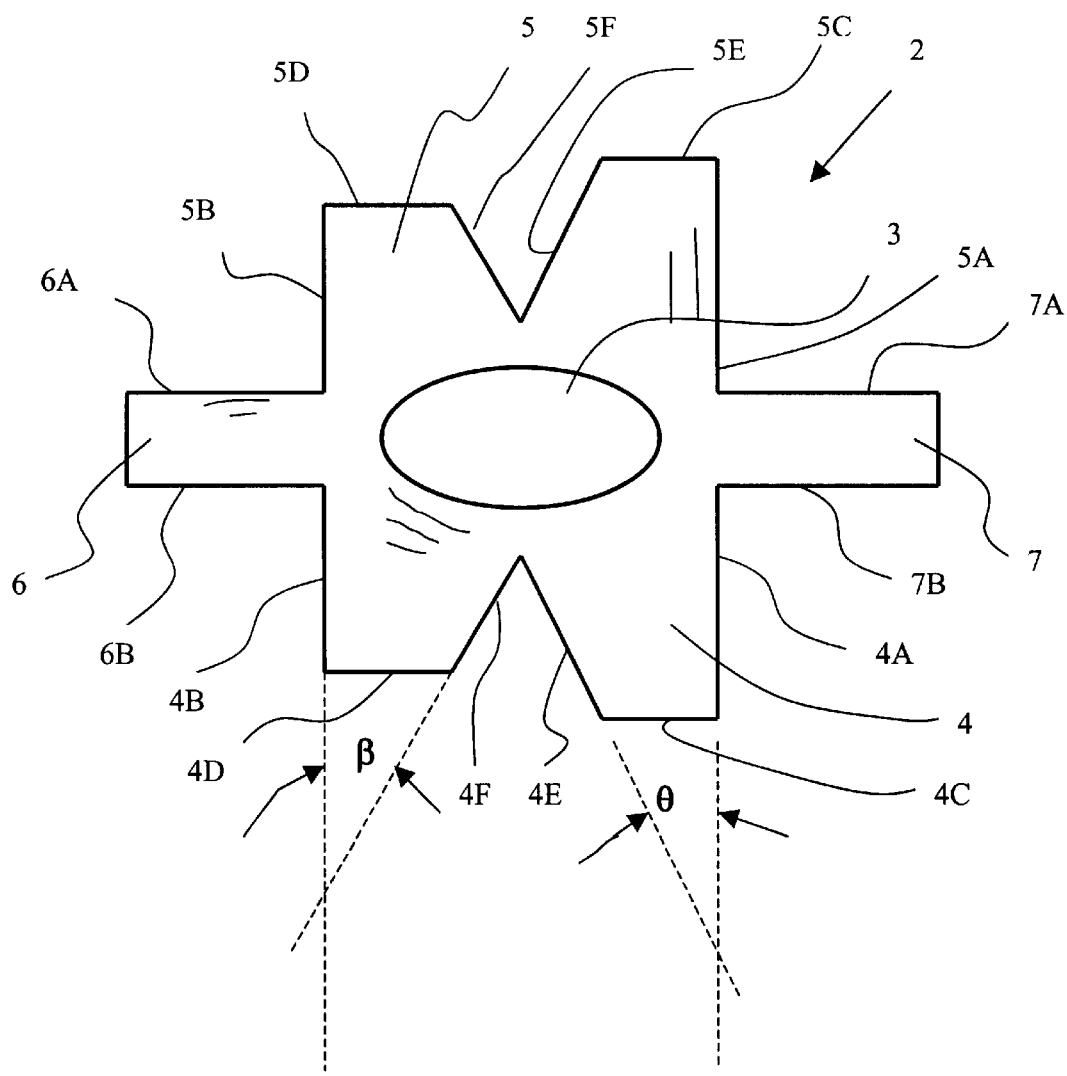
FIG. 3 is another embodiment of the present invention comprising a pre-trimmed singular membrane of biomaterial having a hole at about a central region of the membrane adapted for valve fabrication.

In an alternate embodiment, the singular flexible membrane may be pre-trimmed and shaped for a valve fabrication. FIG. 3 shows another embodiment of the present invention comprising a precut (that is, pre-trimmed) singular membrane 2 of biomaterial having a hole 3 at about a central region of the membrane adapted for valve fabrication. In one illustrative embodiment, the membrane 2 comprises a first major cusp member 4, a second major cusp member 5, a third minor cusp member 6, and a fourth minor cusp member 7. All cusp members are so pre-trimmed that the final fabricated configuration is suitable as a stentless atrioventricular valve apparatus. The first major cusp member 4 has a first side edge 4A, an opposite second side edge 4B, and a first end edge 4C, and a second end edge 4D. Further, the first major cusp member 4 has a first trimmed edge 4E and a second trimmed edge 4F. Similarly as shown in FIG. 3, the second major cusp member 5 has a first side edge 5A, an opposite second side edge 5B, and a first end edge 5C, and a second end edge 5D. Further, the second major cusp member 5 has a first trimmed edge 5E and a second trimmed edge 5F. Not all edges of the major cusp members 4, 5, or the minor cusp members 6, 7 are straight. The edges may be essentially straight or in other suitable curvature suitable for making the intended valve of the present invention.

A first group of the trimmed edges 4E, 5E of the present invention is trimmed and configured at an angle ($\theta$) of about less than 20 degrees from a reference central longitudinal line and adapted to be a constituent of the posterior cusp 51 (as shown in 9). Similarly, the second group of the trimmed edges 4F, 5F of the present invention is trimmed and configured at an angle ($\beta$) of about less than 20 degrees from a reference central longitudinal line and adapted to be a constituent of the anterior cusp 52 (as shown in 9). The angle $\theta$ or $\beta$ may preferably be in the range of about 15 to 20 degrees.

As shown in FIG. 3, the third minor cusp member 6 has two side edges 6A, 6B and an end edge whereas the fourth minor cusp member 7 has two side edges 7A, 7B and an end edge. As stated, any edge may be essentially straight or in other suitable curvature suitable for making the intended valve of the present invention.

Figure 4:
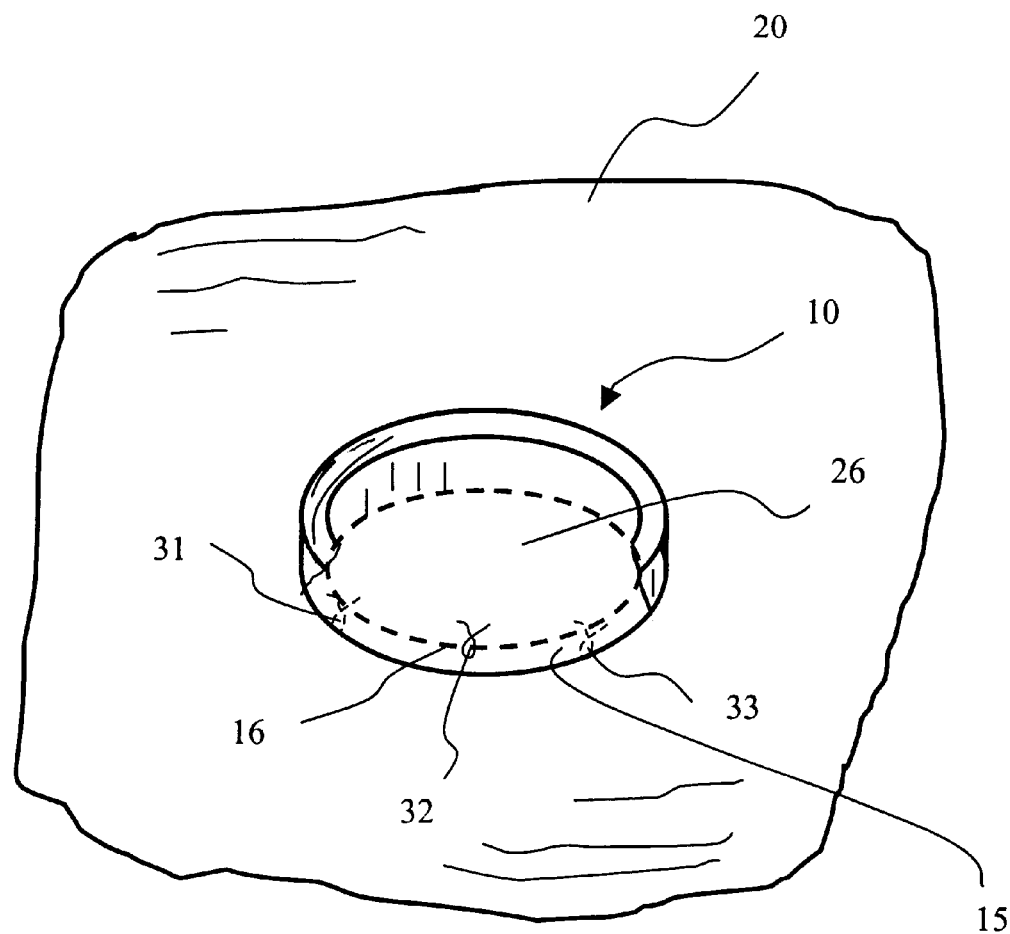
FIG. 4 is a first step of valve fabrication by laying a sewing ring element on top of the singular membrane of biomaterial.

To fabricate a stentless cardiac valve of the present invention, a hole 26 is created at about the center of the membrane 20, wherein the hole 26 (so-called the membrane opening) has a perimeter 27 that substantially matches the second inner edge or perimeter 16 of the ring element 10. FIG. 4 shows a first step of valve fabrication by laying a sewing ring element 10 on top of the singular membrane 20 of biomaterial so as to substantially match the second ring opening 9 against the membrane opening 26. In the alternate fabrication process using a virtual element, this first step is skipped.

A plurality of sutures (either temporary sutures or permanent sutures) 31, 32, 33 or other securing mechanisms to fasten the membrane 20 onto the ring 10 are secured evenly at along the contacting zone between the membrane 20 and the second ring surface 15.

Figure 5:
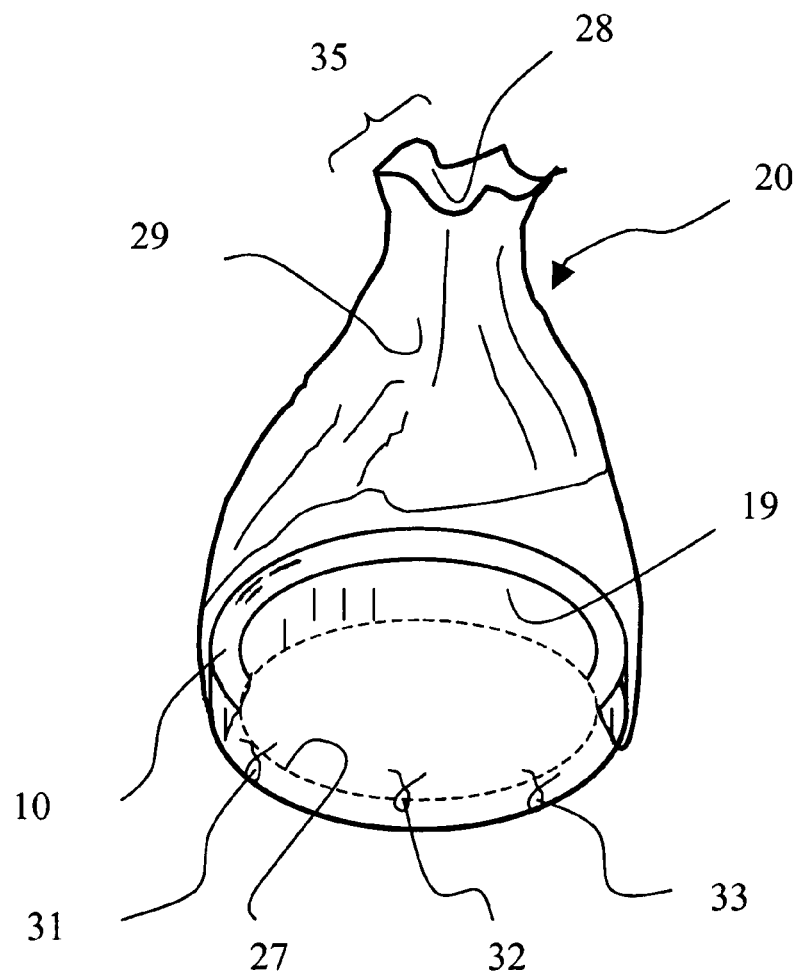
FIG. 5 is a next step of valve fabrication by wrapping a singular membrane around the sewing ring element.

Thereafter, all edges (for example, edges 22, 23, 24, and 25 in FIG. 2; or the cusp members 4, 5, 6, and 7 in FIG. 3) or the periphery region 35 of the membrane 20 are picked up so as to wrap over the second bottom surface 15 of the ring 10 and to continue wrapping around the second outer edges 17, the outer straight side portion 18, and the first outer edge 13 of the sewing ring element 10. In one embodiment, FIG. 5 shows a picked-up membrane with the second membrane surface 29 facing exteriorly while the first membrane surface 28 facing interiorly. The periphery region portion 35 where all edges are picked and pulled close to each other is located at about the very top of the combined structure of the ring element 10 and membrane 20. FIG. 5 shows a next step of the valve fabrication by wrapping a singular membrane around the sewing ring element 10.

Figure 6:
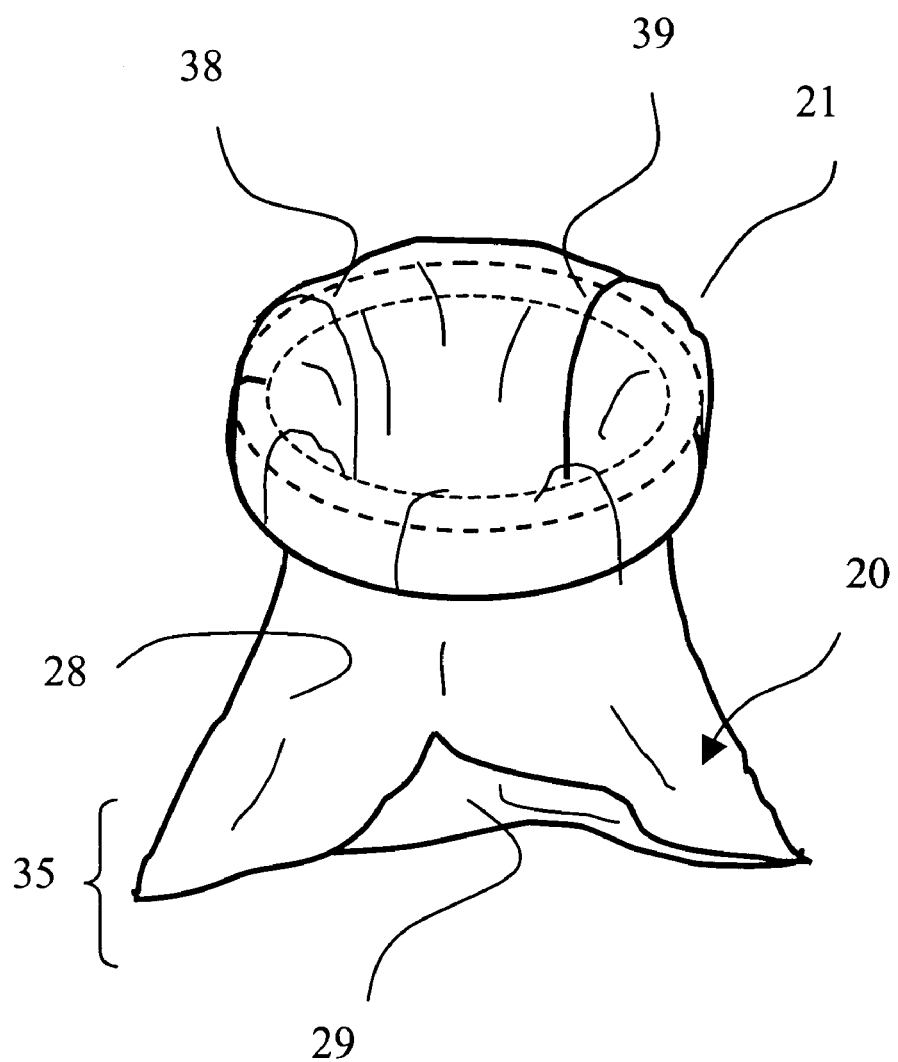
FIG. 6 is a further step of valve fabrication by inverting the periphery of the singular membrane through an opening of the sewing ring element.

FIG. 6 shows a further step of valve fabrication by inverting the periphery 35 of the singular membrane through an opening 11 of the sewing ring element 10 so as to form a complete wrapping around the ring element 10. In other words, the singular membrane 20 hereby wraps over the first surface 12 of the ring element 10 and to continue wrapping around the first inner edge 14 and the second inner edge 16 of the sewing ring element 10. In one embodiment, FIG. 6 shows a fully wrapped membrane with the first membrane surface 28 facing exteriorly while the second membrane surface 29 facing interiorly. The portion of the membrane-covered sewing ring element is also known as the sewing ring 21 of the atrioventricular valve to be secured to the valvular annulus of a patient. There may be a few wrinkles 38, 39 at about the sewing ring 21 as a result of inverting the membrane 20 through the ring element opening 11.

Figure 7:
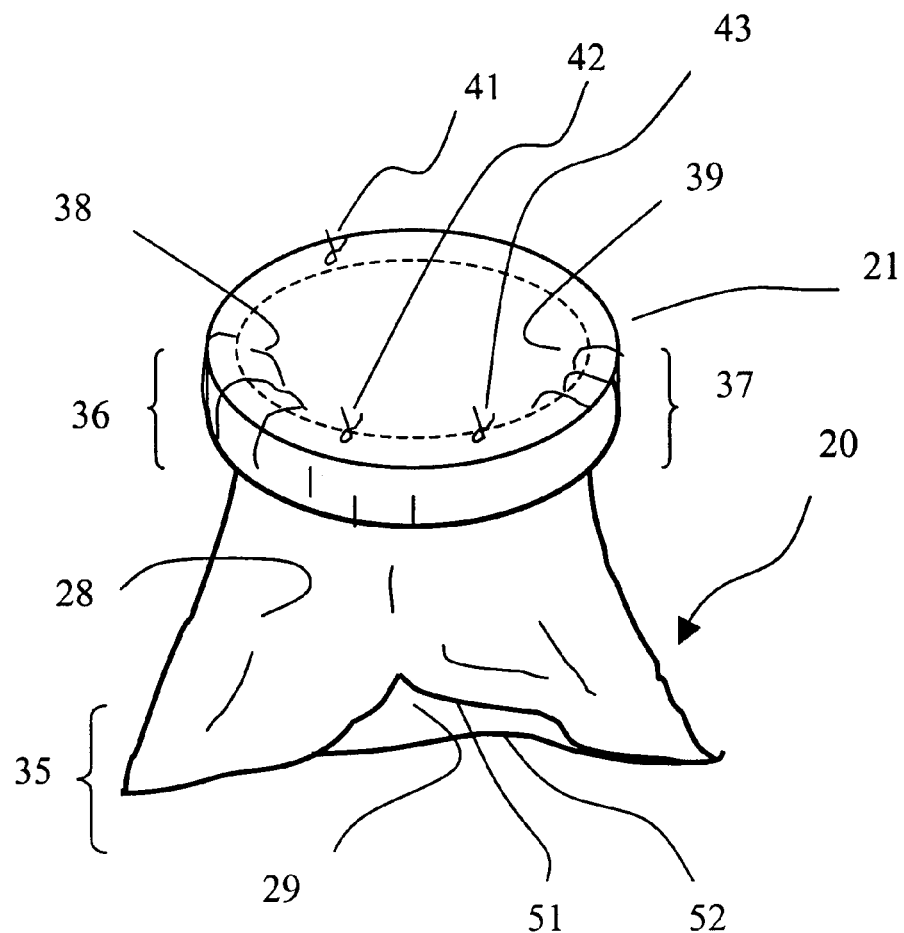
FIG. 7 is another step of valve fabrication by securing the singular membrane onto the sewing ring element.

FIG. 7 shows another step of valve fabrication by securing the singular membrane onto the sewing ring element. To configure the singular membrane 20 more suitable as a functional cardiac valve of the present invention, the membrane 20 is slightly stretched and re-positioned over the ring 10 so that essentially all the wrinkles 38, 39 are grouped at two opposite ends 36, 37 of the ring element 10. In other words, the majority portion of the membrane 20 over the ring element 10 away from the two opposite ends 36, 37 is essentially free of wrinkles.

As shown in FIG. 7, a plurality of sutures 41, 42, 43 or other securing mechanisms are placed substantially equally spaced at along the contacting zone of the membrane and the first ring surface 12. One embodiment of securing the membrane onto the ring element is to suture or stitch the membrane at the second surface 15 to the membrane at the first surface 12 by passing s suture through the ring 10 itself. An alternate embodiment is to subsequently dissolve the ring 10 so that a derived sewing ring 21 is made of the membrane material alone.

Figure 8:
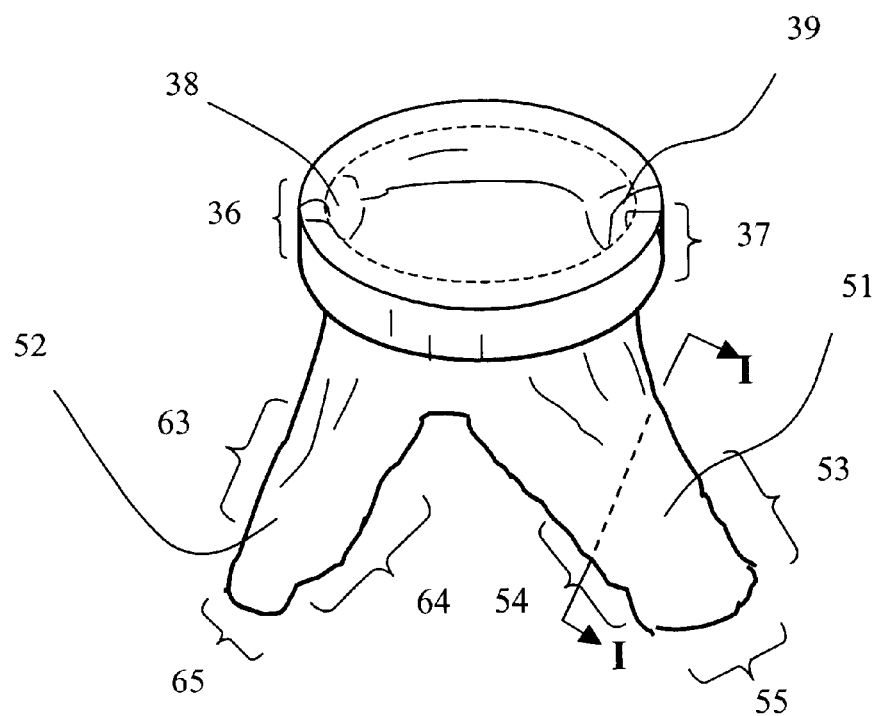
FIG. 8 is one further step of valve fabrication by aligning the potential wrinkles adjacent the remote ends portion of the cusps.
Figure 9:
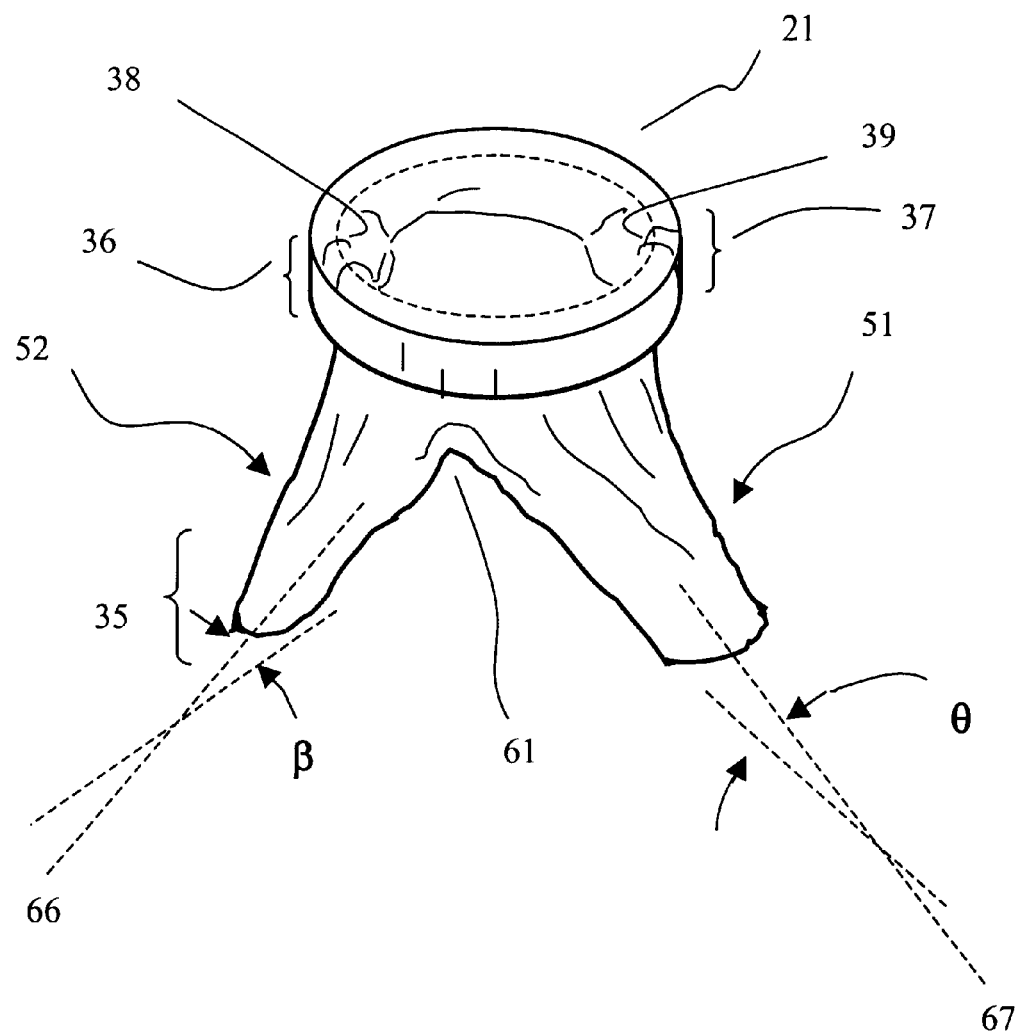
FIG. 9 is still another step of valve fabrication by trimming the cusps at a desired angle with reference to an imaginary central straight line of the cusp, wherein the valve is shown at an open position.

FIG. 8 shows one further step of valve fabrication by aligning the potential wrinkles adjacent the remote ends portion of the cusps, whereas FIG. 9 shows still another step of valve fabrication by trimming the cusps at a desired angle with reference to an imaginary central straight line of the cusp(s). This trimming step may be omitted and substituted by a pre-trimmed singular membrane 2 as shown in FIG. 3.

By following the above-described procedures, a stentless atrioventricular valve can also be fabricated from a pre-trimmed singular membrane 2. The periphery portion (including cusp members 4, 5, 6, and 7) of the membrane 2 is inverted and passes through the ring opening 11 of the sewing ring element 10. The edge pairs (for example, a pair of edges 4B and 6B; a pair of edges 5B and 6A; a pair of edges 5A and 7A; and a pair of edges 4A and 7B) are secured together to form a substantially tubular shape for use as the atrioventricular valve apparatus. In one embodiment, the posterior cusp may comprise the cusp member 7 and its adjacent secured portions of the cusp members 4 and 5. Similarly, the anterior cusp may comprise the cusp member 6 and its adjacent secured portions of the cusp members 4 and 5. The cusp members 4 and 5 are trimmed essentially symmetrical; i.e., the edges 5C, 5D, 5E, and 5F are equivalent counterparts of the edges 4C, 4D, 4E, and 4F, respectively.

FIG. 9 shows a stentless sewing ring 21 with a trimmed membrane. In one illustration of a bi-leaflet valve, the periphery portion 35 is trimmed and configured to include a posterior cusp 51 and an anterior cusp 52. The sewing ring 21 of the present invention comprises an opening defined by a perimeter including at least a first and a second straight side portions thereof. An anterior cusp 52 is configured hinged continuously from the first straight side portion while a posterior cusp 51 is configured hinged continuously from the second straight side portion opposite the anterior cusp 52, wherein the anterior cusp and the posterior cusp are an integral part of a continuum from the singular membrane 20 with a common commissure between remote ends 61 of the anterior cusp 52 and the posterior cusp 51. Collectively, the anterior cusp 52 and the posterior cusp 51 are carried over from the outer surface 18 of the sewing ring element 10 and then hinged continuously along the inner surface 19.

As shown in FIG. 9, the membrane-covered sewing ring 21 is formed by an inverted flange portion of the combined cusps 51, 52 located at about the sewing ring place 21 that is configured to shape the sewing ring opening, wherein the flange portion from the cusps 51, 52 is an integral part of a continuum from the singular membrane 20.

The stentless atrioventricular valve of the present invention may further comprise a third cusp located between the anterior cusp 52 and the posterior cusp 51, wherein the third cusp hinged continuously from a third straight side portion of the perimeter 14 and wherein the third cusp is an integral part of a continuum from the singular membrane 20 without sutured commissure between any two remote ends of the anterior cusp, the posterior cusp and the third cusp. A cardiac valve with two cusps (that is, a bileaflet valve) or three cusps (that is, a trileaflet valve) is well known to an ordinary cardiac surgeon or one who is skilled in the art.

The anterior cusp 52 or the posterior cusp 51 of the stentless atrioventricular valve of the present invention has a generally semicircular or curved edge portion to enable it projecting deeply into the ventricle cavity when the sewing ring 21 is sutured to an atrioventricular junction of a patient heart. In one embodiment as illustrated in FIG. 8, the anterior cusp 52 has a semicircular or curved tip edge 65 and two generally straight side edges 63, 64 that are joined at the tip edge 65, wherein each (63 or 64) of the straight side edges is trimmed and configured at an angle ($\beta$) of about less than 20 degrees from a reference central longitudinal line 66 of the anterior cusp 52 (FIG. 9).

Similarly, in another embodiment as illustrated in FIG. 8, the posterior cusp 51 may have a semicircular or curved tip edge 55 and two generally straight side edges 53, 54 that are joined at the tip edge 55, wherein each of the straight side edges 53, 54 is trimmed and configured at an angle ($\theta$) of about less than 20 degrees from a reference central longitudinal line 67 of the anterior cusp 51 (shown in FIG. 9). The edges at about the cusp joint 61 is so trimmed and configured to exert certain degree of tension for proper valve close and open operations. This tensioned cusp joint 61 is equally true for the case of using a pre-trimmed singular flexible membrane 2.

Figure 10:
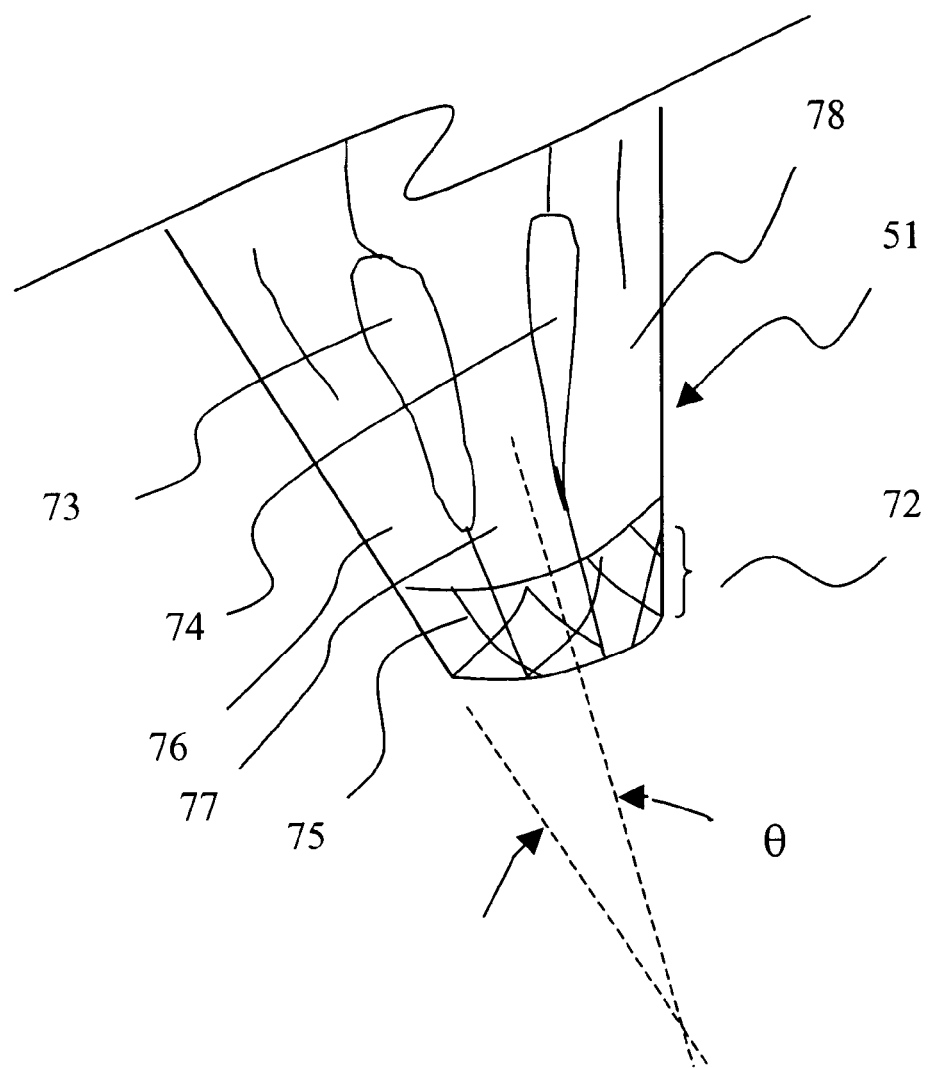
FIG. 10 is a cross-sectional view of section I—I of FIG. 8, illustrating the distal portion of a cusp comprising texture elements at edge portions of the cusps configured to extend the texture elements for connection to papillary muscles in a ventricle cavity when the sewing ring is sutured to an atrioventricular junction of a patient heart.

FIG. 10 shows a cross-sectional view of section I—I of FIG. 8, illustrating the distal portion of a cusp comprising texture elements at edge portion(s) of the cusps configured to extend the texture element(s) for connection to papillary muscles in a ventricle cavity when the sewing ring is sutured to an atrioventricular junction of a patient heart. For illustration purposes, a portion of the posterior cusp 51 is further shown in FIG. 10 to indicate a plurality of optional openings 73, 74 and an end region 72 of the posterior cusp 51 covered with a texture element 75 made of silicone rubber (Silastic™), cloth (usually Dacron™), or cloth coated with polytetrafluoroethylene (Teflon™) or other fabric. A conventional method of securing the texture element onto the cusp may include bonding, stitching, gluing, suturing or the like.

In an alternate embodiment starting with a pre-trimmed singular membrane 2, the cusp member 7, the right-side portion of the cusp member 4, and the right-side portion of the cusp member 5 are to be joined to form the posterior cusp 51 shown in FIG. 10, wherein the cusp members 76, 77, and 78 in FIG. 10 are equivalent counterparts of those referred above. The remote portions 72 of the cusp members 76, 77, 78 are joined by the texture element 75. The remaining portions of the edges of the cusp members 76, 77, 78 away from the remote portions 72 may not secured together and thus may form the openings such as 73, 74.

In securing together the three cusp members of the membrane 2 to form either a posterior cusp or an anterior cusp, more tension is applied to the edge 4E rather than the opposite edge 4A (FIG. 3). This higher tension is generally true for the edges 4F, 5E, and 5F than their corresponding opposite edges 4B, 5A, and 5B, respectively during the valve fabrication process. As a result of appropriate tension arrangements to each individual edge and cusp members, the finished cusp 51 is configured to have lower tension on the cusp member 77 as compared to the adjacent cusp members 76 and 78 and enables the cusps 51, 52 of the present invention to function as a competent atrioventricular heart valve.

The anterior cusp 52 and/or the posterior cusp 51 of the present invention may comprise texture elements at edge portions of the cusps configured to extend the texture elements for connection to papillary muscles in a ventricle cavity when the sewing ring is sutured to an atrioventricular junction of a patient heart. The anatomy of the atrioventricular valves and the subvalvular apparatus of a patient can be found in any medical reference textbook (for example, MITRAL VALVE, edited by H Boudoulas and C F Wooley, published by Futura Publishing, NY 2000). The texture elements are formed integral with the cusps 51, 52 and are provided with integral attachment portions at ends 72 remote from the cusps for suturing to the papillary muscles.

Angelini and associates (*Anatomy of the Mitral Valve* in MITRAL VALVE, edited by H Boudoulas and C F Wooley, published by Futura Publishing, NY 2000), entire contents of which are incorporated herein by reference, teach the mitral valvar complex being attached proximally at the left atrioventricular junction and, distally, through the papillary muscles, to the myocardial wall of the left ventricle. Proper action of the complex depends on normal function and integration of each of the components. Therefore, it is one object of the present invention to provide a stentless atrioventricular valve fabricated from a singular flat membrane of biomaterial adapted to mimic the natural mitral function.

The general configuration of either the posterior cusp 51, the anterior cusp 52 or the third cusp in a trileaflet valve apparatus may be slightly concave to exhibit adequate support when secured to the papillary muscles in a ventricle cavity upon deployment.

Figure 11:
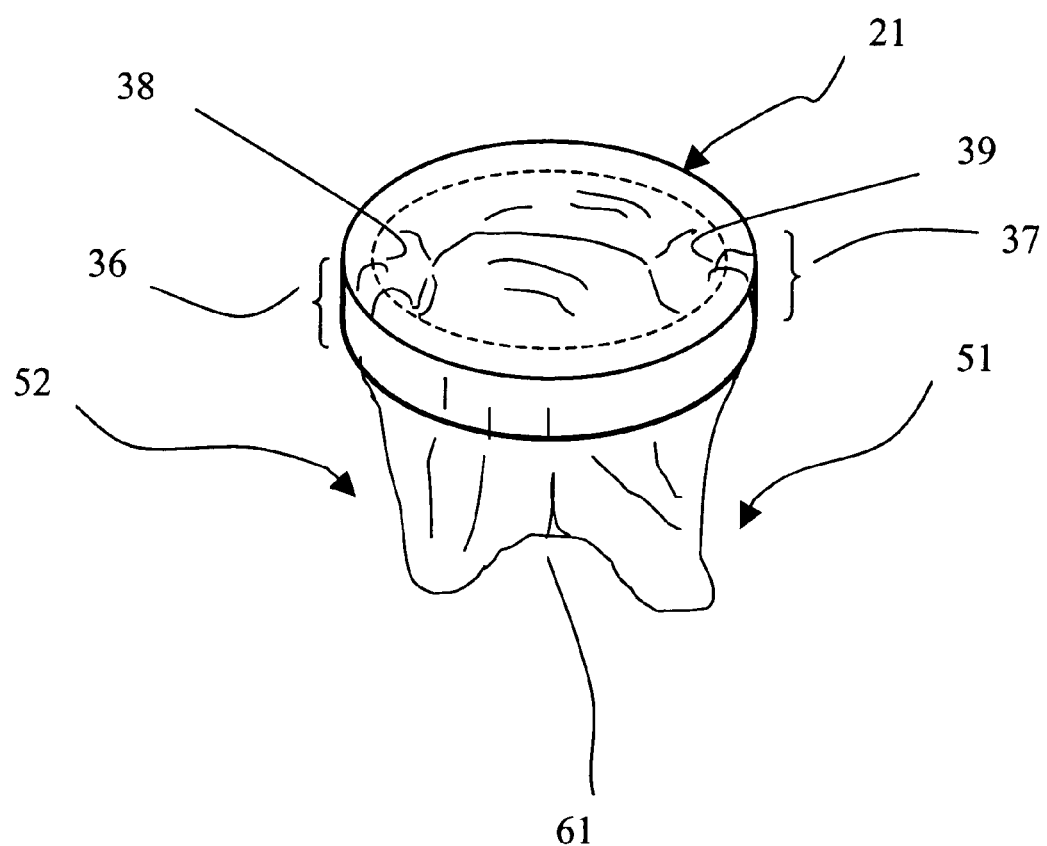
FIG. 11 is the atrioventricular valve shown at a close position.

FIG. 9 shows the stentless atrioventricular valve at an open position while FIG. 11 shows the valve at its close position. At a valve close position, the ventricle is contracted. The cusp is under quite tension because the remote end of the cusps is still attached to the papillary muscle. The cusps joint section 61 so constructed according to the principles of the present invention enables the valve to close promptly at systole.

The present invention discloses a method of forming a stentless atrioventricular valve intended for attaching to a circumferential valve ring and papillary muscles of a patient as afore-mentioned described. The method may comprise the steps of (a) selecting a singular membrane of biomaterial and an essentially flat sewing ring element, wherein said membrane comprises a hole in about a central region of said membrane and a periphery region, and wherein said sewing ring element comprises an outer diameter and an inner diameter defining an inner straight side portion, an outer straight side portion, a bottom side portion and a top side portion, said hole matching said inner diameter of said sewing ring element; (b) placing said sewing ring element on top of said membrane conformed to align said hole with the inner diameter of said ring element; (c) securing said membrane onto said sewing ring element at a contact region of said membrane to the bottom side portion of the ring element; (d) flapping the membrane around the outer straight side portion and the top side portion of said ring element; (e) inserting the periphery of said membrane through the inside diameter of the ring element configured to form a sewing ring with an inverted membrane around all of the bottom side portion, outer straight side portion, top side portion and inner straight side portion; and (f) trimming the membrane to form at least two cusps suitable for replacing in a diseased or dysfunctional atrioventricular valve of the patient.

From the foregoing description, it should now be appreciated that a stentless atrioventricular valve comprising a singular membrane of tissue with at least two cusps, each having two generally straight side edges that are joined at a semicircular tip edge, each straight side edge being trimmed and configured at an angle of about less than 20 degrees from a reference central longitudinal line of the cusp have been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A stentless atrioventricular valve comprising a singular membrane of tissue, said valve having a sewing ring comprising an opening defined by a perimeter including at least a first and a second straight side portions thereof, an anterior cusp hinged continuously from said first straight side portion, a posterior cusp hinged continuously from said second straight side portion opposite said anterior cusp, wherein said anterior cusp and said posterior cusp are an integral part of a continuum from said singular membrane configured to form a substantially tubular shape for use as the atrioventricular valve, wherein the sewing ring is wrapped within the singular membrane of tissue for valve fabrication and wherein the anterior cusp and the posterior cusp further comprise texture elements at edge portions of the cusps configured to extend said texture elements for connection to papillary muscles in a ventricle cavity when the sewing ring is sutured to an atrioventricular junction of a patient heart.

2. The stentless atrioventricular valve of claim 1, wherein the texture elements are made of polyester or polytetrafluoroethylene fabric.

3. The stentless atrioventricular valve of claim 1, wherein the texture elements are formed integral with the cusps and are provided with integral attachment portions at ends remote from the cusps for suturing to the papillary muscles.

* * * * *